US012778909B2

(12) United States Patent
Chun et al.

(10) Patent No.: US 12,778,909 B2
(45) Date of Patent: Nov. 3, 2026

(54) COMPOSITION INCLUDING BENZYLAMINOETHANOL DERIVATIVE AS ACTIVE INGREDIENT FOR PREVENTION OR TREATMENT OF METABOLIC DISEASE

(71) Applicant: JLBIOTHERAPEUTICS, Seoul (KR)

(72) Inventors: Kyung-Hee Chun, Seoul (KR); Jung-Hwan Baek, Seoul (KR)

(73) Assignee: JLBiotherapeutics, Seoul (KR)

( * ) Notice: Subject to any disclaimer, the term of this patent is extended or adjusted under 35 U.S.C. 154(b) by 333 days.

(21) Appl. No.: 18/293,177

(22) PCT Filed: Jul. 28, 2022

(86) PCT No.: PCT/KR2022/011103
§ 371 (c)(1),
(2) Date: Jan. 29, 2024

(87) PCT Pub. No.: WO2023/008919
PCT Pub. Date: Feb. 2, 2023

(65) Prior Publication Data

US 2025/0073185 A1 Mar. 6, 2025

(30) Foreign Application Priority Data

Jul. 30, 2021 (KR) ........................ 10-2021-0100728

(51) Int. Cl.
*A61K 31/137* (2006.01)
*A61P 3/06* (2006.01)
*G01N 33/50* (2006.01)

(52) U.S. Cl.
CPC .............. *A61K 31/137* (2013.01); *A61P 3/06* (2018.01); *G01N 33/5023* (2013.01); *G01N 33/5044* (2013.01)

(58) Field of Classification Search
None
See application file for complete search history.

(56) References Cited

U.S. PATENT DOCUMENTS

| | | | |
|---|---|---|---|
| 2005/0101644 A1 | 5/2005 | Davey et al. | |
| 2023/0104617 A1 | 4/2023 | Wang et al. | |

FOREIGN PATENT DOCUMENTS

| | | |
|---|---|---|
| CN | 112574183 A | 3/2021 |
| CN | 112898314 A | 6/2021 |
| WO | 2021147971 A1 | 7/2021 |

OTHER PUBLICATIONS

International Search Report and Written Opinion (machine translation) in International Patent Application No. PCT/ KR2022/011103, dated Nov. 7, 2022.

Wrigley et al., "Identification and Characterization of Dual Inhibitors of the USP25/28 Deubiquitinating Enzyme Subfamily," ACS Chemical Biology, 12(12), 3113-3125 (2017).

Shibata et al., "Deubiquitylase USP25 prevents degradation of BCR-ABL protein and ensures proliferation of Ph-positive leukemia cells," Oncogene, 39, 3867-3878 (2020).

Kim, Myung Sup et al., Deubiquitinase USP1 enhances CCAAT/ enhancer-biding protein beta (C/EBPB) stability and accelerates adipogenesis and lipid accumulation, Cell Death and disease (2023): 14:776.

*Primary Examiner* — Lauren Wells
(74) *Attorney, Agent, or Firm* — McDonnell Boehnen Hulbert & Berghoff LLP

(57) ABSTRACT

The present invention relates to a pharmaceutical composition and a functional food composition for preventing or treating metabolic disorder, comprising a benzylaminoethanol derivative as an active ingredient. The composition of the present invention shows little or no cytotoxicity while significantly reducing metabolic disorder indicators by significantly inhibiting adipocyte differentiation and lipid accumulation, and thus may be useful as an efficient therapeutic agent for metabolic disorder that has few side effects even upon long-term administration.

8 Claims, 4 Drawing Sheets

Specification includes a Sequence Listing.

SEQUENCE LISTING

```
Sequence total quantity: 6
SEQ ID NO: 1            moltype = DNA  length = 20
FEATURE                 Location/Qualifiers
source                  1..20
                        mol_type = other DNA
                        organism = synthetic construct
SEQUENCE: 1
agggcgatct tgacaggaaa                                              20

SEQ ID NO: 2            moltype = DNA  length = 20
FEATURE                 Location/Qualifiers
source                  1..20
                        mol_type = other DNA
                        organism = synthetic construct
SEQUENCE: 2
cgaaactggc acccttgaaa                                              20

SEQ ID NO: 3            moltype = DNA  length = 20
FEATURE                 Location/Qualifiers
source                  1..20
                        mol_type = other DNA
                        organism = synthetic construct
SEQUENCE: 3
gtgactttga ctacccggga                                              20

SEQ ID NO: 4            moltype = DNA  length = 20
FEATURE                 Location/Qualifiers
source                  1..20
                        mol_type = other DNA
                        organism = synthetic construct
SEQUENCE: 4
ggggctcttg tttgatcacc                                              20

SEQ ID NO: 5            moltype = DNA  length = 20
FEATURE                 Location/Qualifiers
source                  1..20
                        mol_type = other DNA
                        organism = synthetic construct
SEQUENCE: 5
tgggttctag ccagcagagt                                              20

SEQ ID NO: 6            moltype = DNA  length = 20
FEATURE                 Location/Qualifiers
source                  1..20
                        mol_type = other DNA
                        organism = synthetic construct
```

-continued

```
SEQUENCE: 6
accaccagag accgttatgc                                                  20
```

COMPOSITION INCLUDING BENZYLAMINOETHANOL DERIVATIVE AS ACTIVE INGREDIENT FOR PREVENTION OR TREATMENT OF METABOLIC DISEASE

CROSS-REFERENCE TO RELATED APPLICATIONS

This application is a U.S. National Stage Entry of International Patent Application no. PCT/KR2022/011103, filed Jul. 28, 2022, which claims the benefit of priority of Korean Patent Application no. 10-2021-0100728, filed Jul. 30, 2021.

REFERENCE TO AN ELECTRONIC SEQUENCE LISTING

This application contains a Sequence Listing which has been submitted electronically and is hereby incorporated by reference in its entirety. The Sequence Listing was created on Jan. 22, 2024, is named "24-0099-WO-US_Sequence-Listing_ST26" and is 6,380 bytes in size.

TECHNICAL FIELD

The present invention relates to a composition for preventing or treating metabolic disorder comprising, as an active ingredient, a benzylaminoethanol derivative which is an inhibitor of USP25 and USP28.

BACKGROUND ART

Metabolic syndrome, which involves diabetes, hypertension, lipid metabolism abnormalities, and insulin resistance, etc., has emerged as a major group of diseases that threaten human health due to its high prevalence. In developed countries such as the United States and Europe, metabolic syndrome has been considered a serious health problem that threatens national competitiveness, and large amounts of human and material resources have been invested to solve this problem. Diseases belonging to the metabolic syndrome are a group of common diseases that increase the risk of mutual occurrence and are associated with multiple metabolic changes such as aging, stress, and decreased immune function.

According to OECD statistics in 2017, in Korea, the severely obese population is about 5.3% of the total population, which is not high compared to the OECD average obesity rate, but the obesity rate of male children and adolescents (26%, including overweight) is higher than the OECD average (25.6%), and it is predicted that the severely obese population will double by 2030 while the obesity rate tends to increase every year. In addition, socioeconomic losses due to obesity have doubled over the past 10 years to 9.2 trillion won in 2015, and are expected to further accelerate due to aging, etc.

Meanwhile, ubiquitin (Ub) is a 76-amino acid protein that is involved in various intracellular functions such as selective degradation of proteins and regulation of cell division in most eukaryotic organs or cells and is encoded by four genes in humans: UBB, UBC, UBA52, and RPS27A. Ubiquitination refers to the covalent attachment of ubiquitin to substrate proteins via the sequential action of ubiquitin-activating enzyme (E1), ubiquitin-conjugating enzyme (E2), and ubiquitin-conjugating enzyme (E3), and the reversible process of ubiquitination, which removes ubiquitin from substrate proteins, is called deubiquitination.

Deubiquitinases (DUBs), enzymes that triggers deubiquitination, are divided into five families: USP (Ub-specific processing protease), UCH (UbC-terminal hydrolase), Otubain (OTU-domain Ub-aldehyde-binding protein), MJD (Machado-Joseph disease), and JAMM (Jab1/Pad1/MPN domain metallo-enzyme). Among them, USP, which is the largest family, contains, in addition to activation domains such as cysteine box and histidine box, a number of domains whose functions are not yet known. In particular, except for some subtypes, the correlation of USP with metabolic disorders has hardly been studied.

Throughout the specification, a number of publications and patent documents are referred to and cited. The disclosure of the cited publications and patent documents is incorporated herein by reference in its entirety to more clearly describe the state of the related art and the present invention.

DISCLOSURE

Technical Problem

The present inventors have made extensive efforts to develop an efficient therapeutic composition which has few side effects even upon long-term administration while having excellent therapeutic activity against metabolic disorders, including obesity, diabetes, dyslipidemia, fatty liver, and insulin resistance syndrome, and thus is suitable for the treatment of chronic diseases. As a result, the present inventors have found that a benzylaminoethanol derivative compound having a structure of Formula 1, which will be described later, significantly inhibits the differentiation of adipocytes and significantly reduces the amount of lipid accumulation while showing little cytotoxicity, thereby significantly reducing metabolic disorder indicators. Based on this finding, the present invention has been completed.

Therefore, an object of the present invention is to provide a pharmaceutical composition or functional food composition for preventing or treating metabolic disorder.

Another object of the present invention is to provide a method for screening a pharmaceutical composition for preventing or treating metabolic disorder.

Other objects and advantages of the present invention will become more apparent from the following detailed description of the invention, the appended claims and the accompanying drawings.

Technical Solution

In accordance with one aspect of the present invention, the present invention provides a pharmaceutical composition for preventing or treating a metabolic disorder selected from the group consisting of obesity, diabetes, dyslipidemia, fatty liver, and insulin resistance syndrome, comprising a compound represented by following Formula 1 or a pharmaceutically acceptable salt thereof as an active ingredient:

Formula 1

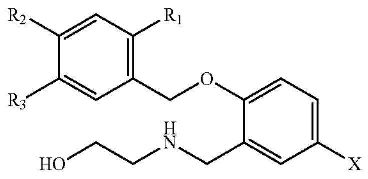

wherein $R_1$ and $R_2$ are each independently hydrogen or halogen, $R_3$ is hydrogen, halogen, or $C_1$-$C_3$ alkyl unsubstituted or substituted with halogen, and X is halogen.

The present inventors have made extensive efforts to develop an efficient therapeutic composition which has few side effects even upon long-term administration while having excellent therapeutic activity against metabolic disorders, including obesity, diabetes, dyslipidemia, fatty liver, and insulin resistance syndrome, and thus is suitable for the treatment of chronic diseases. As a result, the present inventors have found that the benzylaminoethanol derivative having a structure of Formula 1 significantly inhibits the differentiation of adipocytes and significantly reduces the amount of lipid accumulation while showing little cytotoxicity, thereby significantly reducing indicators of metabolic disorders, indicating that it may be used as a composition for efficient treatment of metabolic disorder caused by abnormalities in lipid metabolism.

In the present specification, the term "metabolic disorder" refers to a group of diseases defined by conceptualizing the phenomenon in which risk factors for various cardiovascular diseases and type 2 diabetes caused by metabolic abnormalities are clustered together, and the term is intended to encompass insulin resistance and a variety of complex and diverse metabolic abnormalities and clinical aspects related thereto.

In this specification, the term "obesity" refers to a condition in which energy intake exceeds energy consumption over a long period of time and excess energy is stored as fat, and this level of adipose tissue in vivo becomes excessive. Generally, obesity is clinically defined when the body mass index (=weight (kg)/[height (m)]$^2$) is 25 or more.

In the present specification, the term "diabetes" refers to a chronic disease characterized by relative or absolute deficiency of insulin, resulting in glucose intolerance. Diabetes, which is treated or prevented with the composition of the present invention, includes all types of diabetes, for example, type 1 diabetes, type 2 diabetes, and hereditary diabetes. Type 1 diabetes is insulin-dependent diabetes, which is mainly caused by destruction of β-cells. Type 2 diabetes is non-insulin-dependent diabetes, which is caused by insufficient insulin secretion after meals or by insulin resistance.

In the present specification, the term "dyslipidemia" refers to a pathologic condition in which the fat concentration in the blood is outside the normal range. Examples of dyslipidemia include hypercholesterolemia, hypertriglyceridemia, hypo-HDL-cholesterolemia, and hyper-LDL-cholesterolemia, as well as all abnormal lipid conditions caused by abnormal lipoprotein metabolism.

In the present specification, the term "fatty liver" refers to a condition in which excess lipid accumulates in liver cells due to a disorder of fat metabolism in the liver. Fatty liver is a cause of various diseases such as angina, myocardial infarction, stroke, arteriosclerosis, fatty liver, and pancreatitis.

In the present specification, the term "insulin resistance" refers to a condition in which cells cannot effectively burn glucose due to a decrease in the function of insulin that lowers blood glucose levels. If insulin resistance is high, the human body produces too much insulin, which can lead to hypertension or dyslipidemia as well as heart disease and diabetes. In particular, in type 2 diabetes, the increase in insulin is unrecognized in muscle and fat tissue, and thus insulin action does not occur. The term "insulin resistance syndrome" is a generic term for diseases caused by insulin resistance, and means diseases characterized by cell resistance against insulin action, hyperinsulinemia, increased very-low-density lipoprotein (VLDL) and triglycerides, decreased high-density-lipoprotein (HDL), and hypertension, and the insulin resistance syndrome is usually considered as a risk factor for cardiovascular disease and type 2 diabetes (Reaven G M, Diabetes, 37: 1595-607, (1988)).

In the present specification, the term "alkyl" refers to a straight-chain or branched saturated hydrocarbon group and includes, for example, methyl, ethyl, propyl, isopropyl, etc. The term "$C_1$-$C_3$ alkyl" refers to an alkyl group having an alkyl unit having 1 to 3 carbon atoms, and when the $C_1$-$C_3$ alkyl is substituted, the carbon atom number of the substituent is not included.

In the present specification, the term "halogen" refers to the halogen group elements and includes, for example, fluoro, chloro, bromo, and iodo.

According to a specific embodiment of the present invention, in Formula 1, $R_1$ is hydrogen, $R_2$ is fluoro, $R_3$ is $C_1$-$C_3$ alkyl substituted with halogen, and X is bromine.

More specifically, $R_3$ is trifluoromethyl.

The compound of Formula 1, wherein $R_1$ is hydrogen, $R_2$ is fluoro, $R_3$ is trifluoromethyl, and X is bromine, is a compound having the IUPAC name "2-(5-bromo-2-(4-fluoro-3-(trifluoromethyl)benzyloxy)benzylamino)ethanol" (CAS number: 2165322-94-9) and is also called "AZ1". The compound is known to have dual inhibitory activity against ubiquitin specific protease (USP) 25 and USP 28, and thus has been suggested to have a therapeutic effect against several cancer types, but the relationship thereof with metabolic disorders is not known at all.

In the present specification, the term "pharmaceutically acceptable salt" includes a salt derived from a pharmaceutically acceptable inorganic acid, organic acid, or base. Examples of suitable acids include hydrochloric acid, hydrobromic acid, sulfuric acid, nitric acid, perchloric acid, fumaric acid, maleic acid, phosphoric acid, glycolic acid, lactic acid, salicylic acid, succinic acid, toluene-p-sulfonic acid, tartaric acid, acetic acid, trifluroacetic acid, citric acid, methanesulfonic acid, formic acid, benzoic acid, malonic acid, naphthalene-2-sulfonic acid, benzenesulfonic acid, and the like. Salts derived from suitable bases include salts of alkali metals such as sodium, alkaline earth metals such as magnesium, ammonium, and the like.

According to a specific embodiment of the present invention, the dyslipidemia is hyperlipidemia.

The term "hyperlipidemia" as used in the present specification refers to a disease which occurs when metabolism of fats such as triglycerides and cholesterol is poor and lipid levels in the blood are maintained at high levels. More specifically, hyperlipidemia refers to a state in which lipid components such as triglycerides, LDL cholesterol, phospholipids, and free fatty acids in the blood are increased. Hyperlipidemia includes hypercholesterolemia or hypertriglyceridemia, which occurs with a high incidence.

According to a specific embodiment of the present invention, the fatty liver is non-alcoholic fatty liver.

In the present specification, the term "non-alcoholic fatty liver (NAFL)" refers to a disease in which excess lipid accumulates in liver cells regardless of the uptake of alcohol, and includes simple fatty liver (steatosis) and non-alcoholic steatohepatitis (NASH). Simple fatty liver has a good clinical prognosis, but NASH, accompanied by inflammation or fibrosis, is a progressive liver disease and is recognized as a precursor disease that causes cirrhosis or liver cancer. Obesity and insulin resistance are representative risk factors for non-alcoholic fatty liver disease. Risk factors for the progression of liver fibrosis include obesity (BMI>30), ratio of liver function parameters detected in serum (AST/ALT>1), and diabetes. Particularly, when hepatitis C carriers have non-alcoholic fatty liver, the non-alcoholic fatty liver can progress to liver cancer. 69 to 100% of patients with non-alcoholic fatty liver disease are obese, and 20 to 40% of obese patients have non-alcoholic fatty liver disease. In particular, 10 to 77% of obese children in Europe, the United States, and Asia have non-alcoholic fatty liver lesions, because obesity is the most important risk factor for non-alcoholic liver disease.

In the present specification, the term "prevention" means inhibiting the occurrence of a disorder or a disease in a subject who has never been diagnosed as having the disorder or disease, but is likely to suffer from such disorder or disease.

In the present specification, the term "treatment" means (a) inhibiting the progress of a disorder, disease or symptom; (b) alleviating the disorder, disease or symptom; or (c) eliminating the disorder, disease or symptom. When the composition of the present invention is administered to a subject, it binds directly to TUFM, thereby functioning to activate the influx of autophagy and induce lipolysis, thus suppressing the development of metabolic disorder symptoms due to excessive accumulation of fat, or eliminating or alleviating metabolic disorder symptoms. Thus, the composition of the present invention may serve as a therapeutic composition for the disorder alone, or may be administered in combination with other pharmacological ingredients and applied as a therapeutic aid for the disorder. Accordingly, as used in the present specification, the term "treatment" or "therapeutic agent" encompasses "treatment aid" or "therapeutic aid agent".

In the present specification, the term "administration" or "administering" means administering a therapeutically effective amount of the composition of the present invention directly to a subject so that the same amount is formed in the subject's body.

In the present specification, the term "therapeutically effective amount" refers to an amount of the composition containing a pharmacological ingredient sufficient to provide a therapeutic or prophylactic effect to a subject to whom the pharmaceutical composition of the present invention is to be administered. Accordingly, the term "therapeutically effective amount" encompasses a "prophylactically effective amount".

In the present specification, the term "subject" includes, without limitation, humans, mice, rats, guinea pigs, dogs, cats, horses, cows, pigs, monkeys, chimpanzees, baboons or rhesus monkeys. Specifically, the subject of the present invention is a human.

When the composition of the present invention is prepared as a pharmaceutical composition, the pharmaceutical composition of the present invention comprises a pharmaceutically acceptable carrier.

Examples of the pharmaceutically acceptable carrier that is comprised in the pharmaceutical composition of the present invention include, but are not limited to, lactose, dextrose, sucrose, sorbitol, mannitol, starch, gum acacia, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, and mineral oil, which are commonly used in formulation. The pharmaceutical composition of the present invention may further comprise a lubricant, a wetting agent, a sweetening agent, a flavoring agent, an emulsifying agent, a suspending agent, a preservative, and the like, in addition to the above-described components. Suitable pharmaceutically acceptable carriers and agents are described in detail in Remington's Pharmaceutical Sciences ($19^{th}$ ed., 1995).

The pharmaceutical composition of the present invention may be administered orally or parenterally. Specifically, it may be administered parenterally. More specifically, it may be administered subcutaneously or transdermally An appropriate dosage of the pharmaceutical composition of the present invention may vary depending on various factors such as formulation method, administration mode, patient's age, weight, sex, pathological condition, diet, administration time, administration route, excretion rate, and reaction sensitivity. A preferred dosage of the pharmaceutical composition of the present invention is within the range of 0.001 to 100 mg/kg for an adult.

The pharmaceutical composition of the present invention may be prepared in a unit dose form or prepared to be contained in a multi-dose container by formulating with a pharmaceutically acceptable carrier and/or excipient, according to a method that may be easily carried out by a person skilled in the art. Here, the formulation of the pharmaceutical composition may be a solution, suspension, syrup or emulsion of the pharmaceutical composition in oil or aqueous medium, or an extract, powder, granule, tablet or capsule containing the pharmaceutical composition, and may further comprise a dispersing agent or a stabilizer.

In accordance with another aspect of the present invention, the present invention provides a food composition for ameliorating or alleviating a metabolic disorder selected from the group consisting of obesity, diabetes, dyslipidemia, fatty liver, and insulin resistance syndrome, comprising a compound represented by following Formula 1 or a sitologically acceptable salt thereof as an active ingredient:

Formula 1

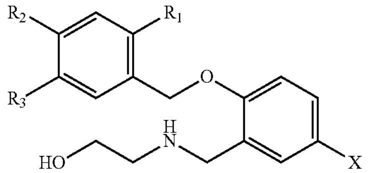

wherein $R_1$ and $R_2$ are each independently hydrogen or halogen, $R_3$ is hydrogen, halogen, or $C_1$-$C_3$ alkyl unsubstituted or substituted with halogen, and X is halogen.

Since the compound of Formula 1 used in the present invention and the liver disease to be ameliorated using the compound have already been described above, description thereof will be omitted to avoid excessive overlapping In the present specification, the term "sitologically acceptable salt" refers to a salt in a form that may be used in a food composition, among salts composed of cations and anions bound together by electrostatic attraction, and specific examples thereof include examples of the above-described "pharmaceutically acceptable salts".

When the composition of the present invention is prepared as a food composition, it may comprise not only the compound of the present invention as an active ingredient, but also carbohydrates, seasonings, and flavoring agents, which are commonly added in food preparation. Examples of the carbohydrates include, but are not limited to, monosaccharides such as glucose and fructose, disaccharides such as maltose and sucrose, polysaccharides such as dextrins and cyclodextrins, and sugar alcohols such as xylitol, sorbitol, and erythritol. Examples of the flavoring agents include natural flavoring agents [thaumatin, stevia extract (e.g., rebaudioside A, glycyrrhizin, etc.)] and synthetic flavoring agents (saccharin, aspartame, etc.). For example, when the food composition of the present invention is prepared as a drink, it may further comprise, in addition to a pine bark extract as an active ingredient of the present invention, citric acid, liquid fructose, sugar, glucose, acetic acid, malic acid, fruit juice, eucommia extract, jujube extract, licorice extract, or the like.

In accordance with still another aspect of the present invention, the present invention provides a method for preventing or treating a metabolic disorder selected from the group consisting of obesity, diabetes, dyslipidemia, fatty liver, and insulin resistance syndrome, comprising a step of administering to a subject a pharmaceutical composition composition comprising a compound represented by Formula 1 below or a pharmaceutically acceptable salt thereof as an active ingredient.

Formula 1

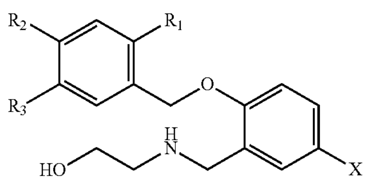

Since the compound of Formula 1 used in the present invention and the liver disease to be ameliorated using the compound have already been described above, description thereof will be omitted to avoid excessive overlapping.

In accordance with yet another aspect of the present invention, the present invention provides a method for ameliorating or alleviating a metabolic disorder selected from the group consisting of obesity, diabetes, dyslipidemia, fatty liver, and insulin resistance syndrome, comprising a step of administering to a subject a food composition comprising a compound represented by Formula 1 below or a sitologically acceptable salt thereof as an active ingredient.

Formula 1

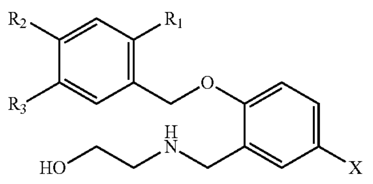

wherein $R_1$ and $R_2$ are each independently hydrogen or halogen, $R_3$ is hydrogen, halogen, or $C_1$-$C_3$ alkyl unsubstituted or substituted with halogen, and X is halogen.

Since the compound of Formula 1 used in the present invention and the liver disease to be ameliorated using the compound have already been described above, description thereof will be omitted to avoid excessive overlapping.

In accordance with still yet another aspect of the present invention, the present invention provides a method for screening a pharmaceutical composition for preventing or treating a metabolic disorder selected from the group consisting of obesity, diabetes, dyslipidemia, fatty liver, and insulin resistance syndrome, the method comprising steps of.

(1) bringing a test substance into contact with a biological sample containing cells expressing a deubiquitinase selected from the group consisting of ubiquitin-specific protease (USP) 25, USP28, and a combination thereof; and (2) measuring the activity or expression level of the deubiquitinase in the sample, wherein, when the activity or expression level of the deubiquitinase decreased, the test substance is determined as the composition for preventing or treating a metabolic disorder.

The correlation between metabolic disorders caused by abnormal lipid metabolism, such as obesity, and the USP25 or USP28 enzyme, is not yet known. According to the present invention, the present inventors have suggested for the first time that the USP25 and USP28 enzymes can be a therapeutic target for metabolic disorders, by observing that the compound of the present invention, which has been reported to have inhibitory activity against USP25 and USP28, inhibits adipocyte differentiation and reduces lipid accumulation.

According to the screening method of the present invention, a test substance is first brought into contact with a biological sample containing cells expressing USP25 and/or USP28. In the present invention, the term "biological sample" is any sample containing cells expressing USP25 and/or USP28, obtained from mammals, including humans, and includes, but is not limited to, tissues, organs, cells, or cell cultures. Specifically, the biological sample includes adipocytes or a culture thereof.

The term "test substance" used while referring to the screening method of the present invention refers to an unknown substance that is used in screening to examine whether or not it affects the activity or expression level of USP25/28 at the gene or protein level. Examples of the test substance include, but are not limited to, compounds, nucleotides, antibodies, antisense-RNA, small interference RNA (siRNA), and natural product extracts. Subsequently, the expression level or activity of USP25 and/or USP28 in the biological sample treated with the test substance is measured. The measurement of the expression level may be performed by various immunoassay methods known in the art or by various gene detection methods using specifically designed primers or probes targeting a gene whose sequence is known. As a result of the measurement, when the expression level or activity of USP25 and/or USP28 decreased, the test substance may be determined as a composition for preventing or treating metabolic disorder.

In the present specification, the term "decrease in expression level or activity" means that the expression level or unique in vivo function of USP25 and/or USP28 decreases to the extent that various lipid metabolism indicators, including body weight, body fat mass, liver lipid weight, and white fat weight, are reduced to measurable levels. A decrease in the activity includes not only a simple decrease in function but also an ultimate decrease in the activity due to a decrease in stability. Specifically, the term "decrease in expression level or activity" may mean a state in which the activity or expression level decreased by at least 20%, more specifically at least 40%, even more specifically at least 60%, compared to the control group.

Advantageous Effects

The features and advantages of the present invention are summarized as follows:

(a) The present invention provides a pharmaceutical composition and a functional food composition for preventing or treating metabolic disorder, comprising a benzylaminoethanol derivative as an active ingredient.

(b) The composition of the present invention shows little or no cytotoxicity while significantly reducing metabolic disorder indicators by significantly inhibiting adipocyte differentiation and lipid accumulation, and thus may be useful as an efficient therapeutic agent for metabolic disorder that has few side effects even upon long-term administration.

MODE FOR INVENTION

Figure 1:
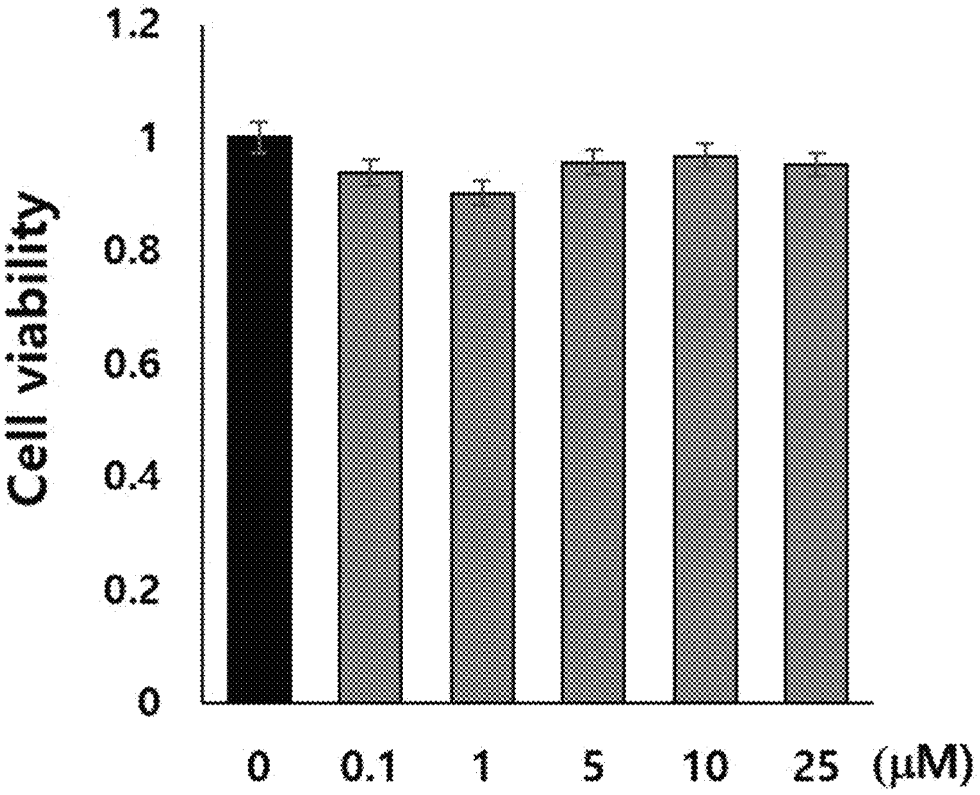
FIG. 1 shows the results of analyzing the viability of 3T3-L1 cells treated with 0, 0.1 1, 5, 10 and 25 μM of an AZ1 compound and untreated control cells.

Hereinafter, the present invention will be described in more detail with reference to examples. These examples are only for explaining the present invention in more detail, and it will be apparent to those skilled in the art that the scope of the present invention according to the subject matter of the present invention is not limited by these examples.

EXAMPLES

Experimental Methods

Cytotoxicity Measurement

3T3-L1 cells were seeded in a 96-well plate with DMEM (Welgene) containing 10% bovine calf serum (Gibco) and 1% penicillin-streptomycin (Gibco), and cultured in an incubator for 24 hours at 37° C. under 5% $CO_2$. Next, the cells were treated with the AZ1 compound at concentrations of 0, 0.1, 1, 5, 10 and 25 μM. After 48 hours, 10 μl of EZ-Cytox was added to each cell culture which was then incubated for 30 minutes, and the absorbance at 450 nm was measured using a microplate reader.

Analysis of Adipocyte Differentiation

3T3-L1 cells were seeded in a 6-well plate at a cell density of $6\times10^4$ cells/well with DMEM (Welgene) containing 10% bovine calf serum (Gibco) and 1% penicillin-streptomycin (Gibco), and cultured in an incubator for 48 hours at 37° C. under 5% $CO_2$. When the cell confluence reached 100%, the existing medium was removed, fresh DMEM (10% bovine calf serum, and 1% penicillin-streptomycin) was added, and the cells were cultured for another 48 hours. Then, the existing culture medium was removed again and the cells were treated with DMEM (10% fetal bovine serum (Gibco), and 1% streptomycin) containing differentiation-inducing substances (insulin, dexamethasone, and 3-isobutyl-1-methylxanthine) and AZ1 (0, 0.1, 1, 5, 10, and 25 μM). After 48 hours, the medium was replaced with DMEM (10% fetal bovine serum (Gibco), and 1% streptomycin) containing insulin and AZ1 (0, 0.1, 1, 5, 10, and 25 μM). After 48 hours, the medium was replaced again with DMEM (10% fetal bovine serum (Gibco), and 1% streptomycin) containing AZ1 (0, 0.1, 1, 5, 10, and 25 μM). After 48 hours, when differentiation was completed, the cells were collected and used for gene and protein expression analysis.

Adipocyte Staining and Lipid Accumulation Measurement

After completion of differentiation, the medium of the 3T3-L1 cells was removed, and the cells were washed with PBS and fixed with 10% formalin for 20 minutes. After removing formalin, the plate was washed with distilled water and then dried. A 100% Oil-Red-O stock solution was prepared by dissolving Oil-Red-O (Sigma) in 100% isopropanol, and then mixed with distilled water to prepare a 60% Oil-Red-O solution. The cells were treated with the 60% Oil-Red-O solution and incubated for 30 minutes. After completion of staining, the cells were washed three times with distilled water. Thereafter, the cells were treated with 100% isopropanol to dissolve the Oil-Red-O dye, and then the absorbance at 500 nm was measured using a microplate reader.

Measurement of Gene Expression

After completion of differentiation, the 3T3-L1 cells were treated with 1 ml of Easy blue (Intron) and then minced using a homogenizer. 200 μl of chloroform was added to and mixed well with the cells, and the mixture was incubated for 3 minutes and then centrifuged at 13,200 rpm for 15 minutes at 4° C. After centrifugation, only the supernatant was transferred to a fresh tube, and the same amount of isopropyl alcohol was added thereto and mixed well therewith. After incubation for 10 minutes, centrifugation was performed at 13,200 rpm for 10 minutes at 4° C. After removing the supernatant, the RNA pellet was washed with 70% ethanol and centrifuged at 13,200 rpm for 5 minutes at 4° C. After removing the supernatant and drying the RNA pellet for 10 minutes, the RNA pellet was dissolved in RNAase-free water.

cDNA was synthesized from the extracted RNA using ReverTraAce RT master mix (TOYOBO), and then gene expression changes were measured using a real-time PCR system (ABI). The primer sets used are summarized in Table 1 below.

TABLE 1

| Gene | Direction | Primer sequence |
|---|---|---|
| PPARg | Forward | 5'-AGGGCGATCTTGACAGGAAA-3' |
| PPARg | Reverse | 5'-CGAAACTGGCACCCTTGAAA-3' |
| C/EBPa | Forward | 5'-GTGACTTTGACTACCCGGGA-3' |
| C/EBPa | Reverse | 5'-GGGGCTCTTGTTTGATCACC-3' |
| FASN | Forward | 5'-TGGGTTCTAGCCAGCAGAGT-3' |
| FASN | Reverse | 5'-ACCACCAGAGACCGTTATGC-3' |

Measurement of Protein Expression

After completion of differentiation, the 3T3-L1 cells were added to RIPA buffer (Biosesang), collected in a 1.5-ml EP-tube, and then lysed. The cell lysate was incubated on ice for 20 minutes and then centrifuged at 13,200 rpm for 25 minutes at 4° C. After centrifugation, the supernatant was transferred to a fresh EP-tube, and then the amount of the protein contained in the supernatant was quantified using Bradford reagent (Thermo Fisher Scientific). An equal amount of protein was placed in a fresh EP-tube, and 5×SDS sample buffer was added thereto and the mixture was heated at 100° C. for 5 minutes, thereby preparing a sample to be used for Western blotting. The protein sample was electrophoresed on an SDS polyacrylamide gel and then transferred to a PVDF membrane (Merck). The PVDF membrane was blocked with 5% skim milk for 1 hour, and then primary antibody (Santacruz) was added to 5% BSA solution and poured onto the membrane which was then subjected to O/N reaction at 4° C. After washing with PBST three times for 10 minutes each, 5% skim milk containing secondary antibody (Bethyl) was added to the membrane which was then incubated for 1 hour. Thereafter, the membrane was washed three times with PBST for 10 minutes each, and then the membrane was incubated with ECL solution (Bio-Rad), and the protein was detected using LAS (Vilber).

Experimental Results

Cytotoxicity Measurement (WST Assay)

There was no significant difference in viability between the cells treated with 0, 0.1, 1, 5, 10, and 25 μM of the AZ1 compound and untreated cells (FIG. 1). Accordingly, it was confirmed that AZ1 did not exhibit cytotoxicity at all the treatment concentrations.

Adipocyte Staining and Lipid Accumulation Measurement

Figure 2A:
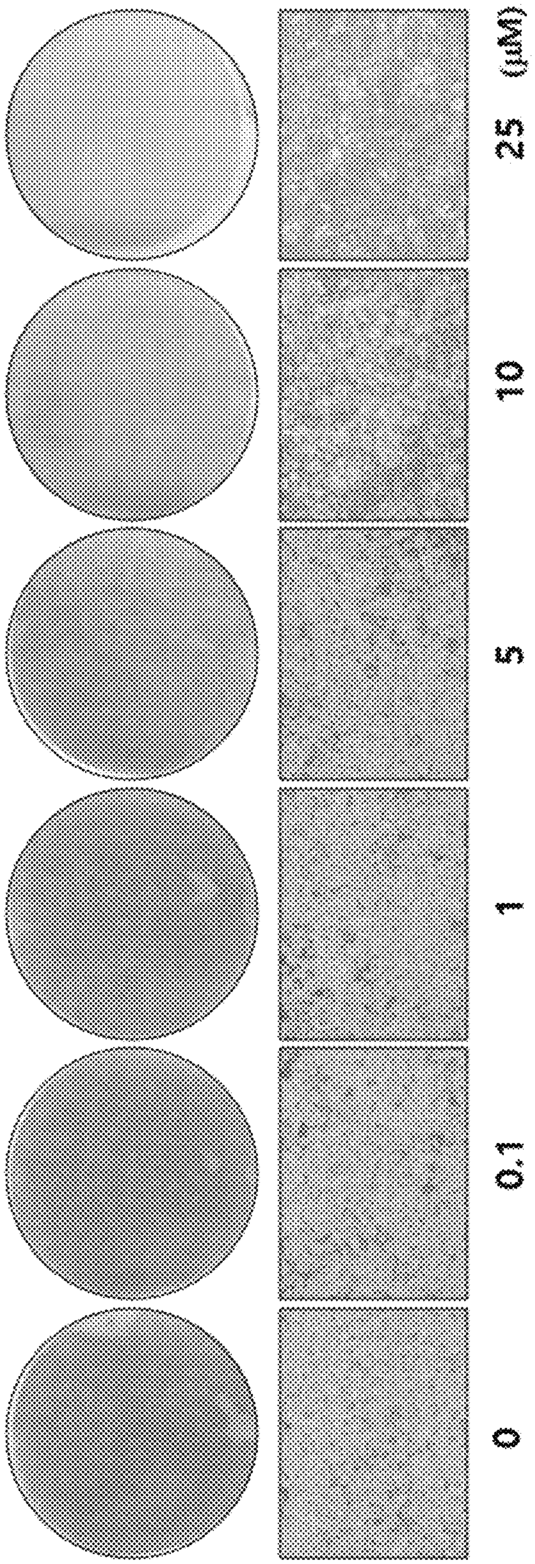
FIG. 2 shows the results of observing adipocyte differentiation by Oil-Red-O staining (FIG. 2A) and measuring the amount of lipid accumulation (FIG. 2B), after treating 3T3-L1 cells with the AZ1 compound.
Figure 2B:
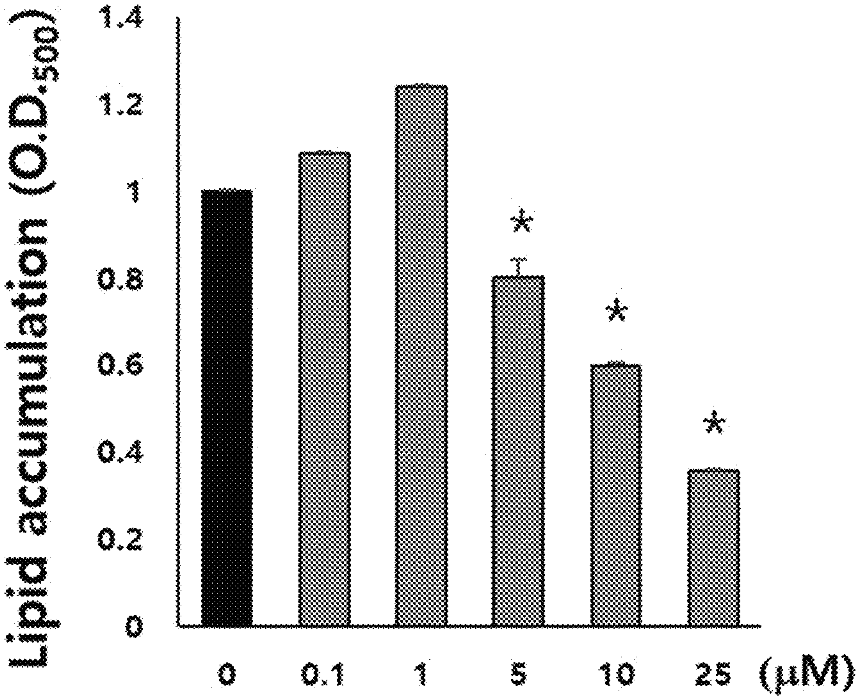

As a result of Oil-Red-O staining of the 3T3-L1 cells, it was confirmed that adipocyte differentiation of the cells treated with 5 μM or more of AZ1 was significantly reduced compared to that of untreated cells (FIG. 2A). In addition, at concentrations of 5 μM or higher, AZ1 reduced lipid accumulation in a concentration-dependent manner (FIG. 2B).

Measurement of Gene and Protein Expression Levels

Figure 3A:
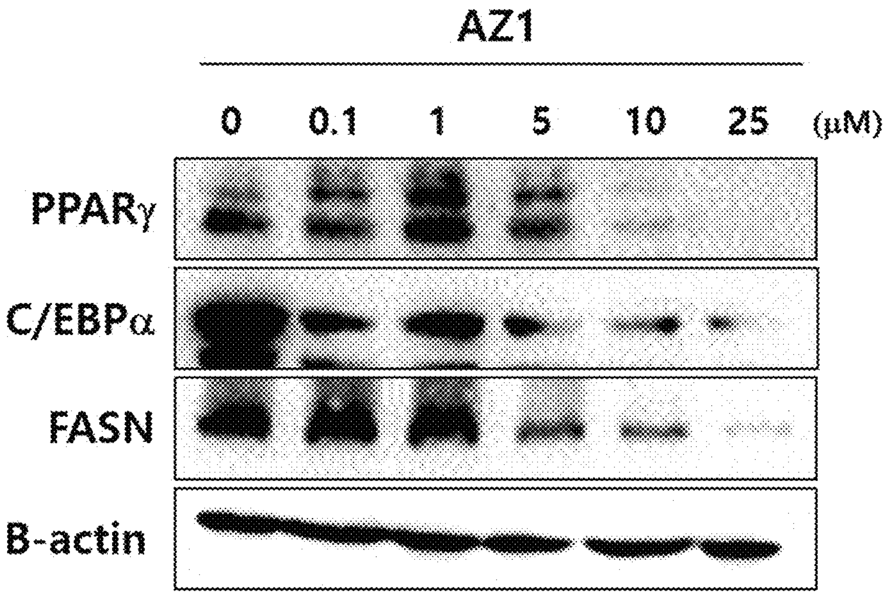
FIG. 3 shows the results of measuring the protein expression levels (FIG. 3A) and mRNA expression levels (FIG. 3B) of PPARg, C/EBPa, and FASN, which are factors related to adipocyte differentiation and lipid accumulation, after treating 3T3-L1 cells with the AZ1 compound.
Figure 3B:
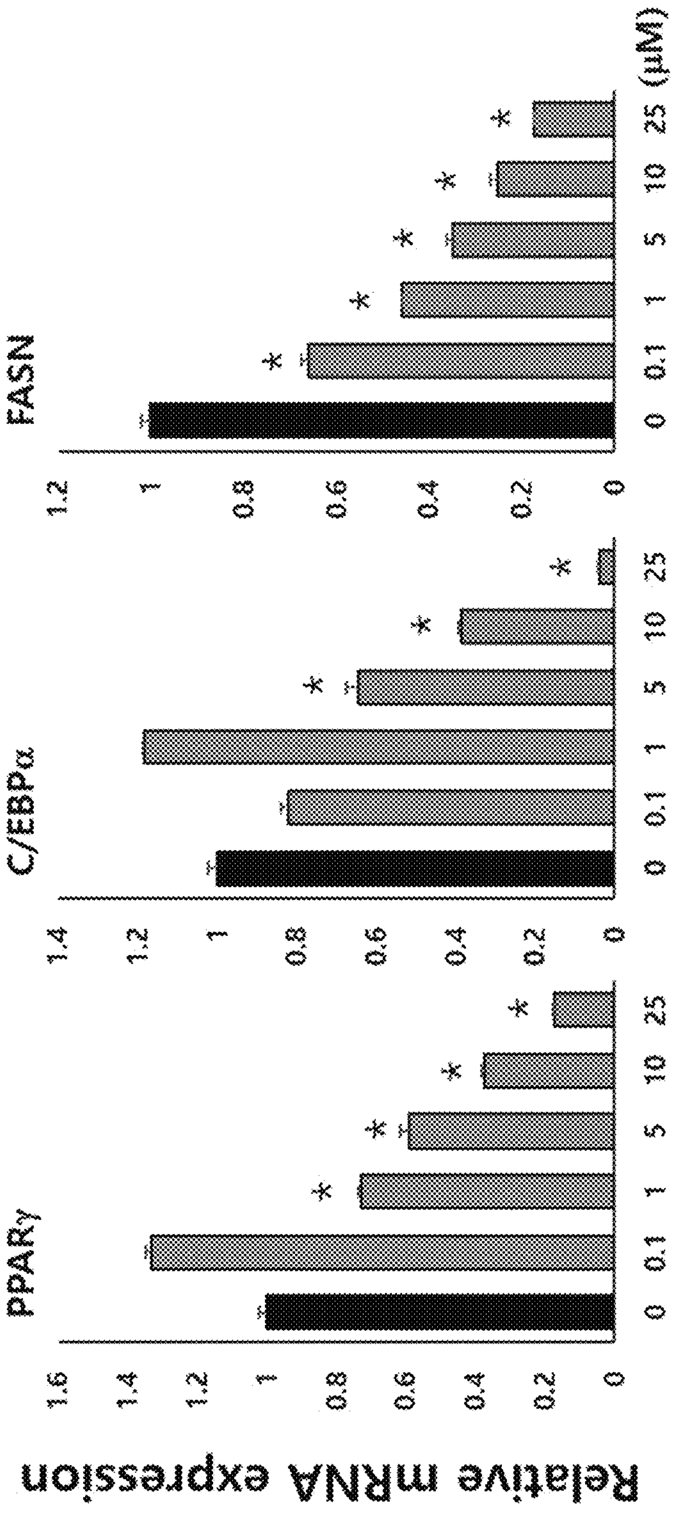

It was confirmed that all the protein expression levels (FIG. 3A) and mRNA expression levels (FIG. 3B) of PPARg, C/EBPa, and FASN, which are factors related to adipocyte differentiation and lipid accumulation, were significantly reduced in the 3T3-L1 cells treated with 5 μM or higher of AZ1 in a concentration-dependent manner compared to the control group untreated with AZ1.

Although the present invention has been described in detail with reference to the specific features, it will be apparent to those skilled in the art that this description is only of a preferred embodiment thereof, and does not limit the scope of the present invention. Thus, the substantial scope of the present invention will be defined by the appended claims and equivalents thereto.

The invention claimed is:

1. A method for preventing or treating a metabolic disorder selected from the group consisting of obesity, diabetes, dyslipidemia, fatty liver, and insulin resistance syndrome, the method comprising administering to a subject in need thereof a pharmaceutical composition comprising a compound represented by Formula 1 or a pharmaceutically acceptable salt thereof as an active ingredient:

Formula 1

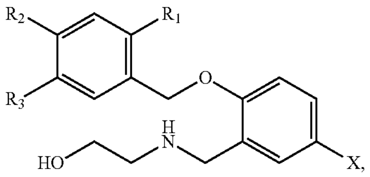

wherein $R_1$ and $R_2$ are each independently hydrogen or halogen, $R_3$ is hydrogen, halogen, or $C_1$-$C_3$ alkyl unsubstituted or substituted with halogen, and X is halogen.

2. The method according to claim 1, wherein, in Formula 1, $R_1$ is hydrogen, $R_2$ is fluoro, $R_3$ is $C_1$-$C_3$ alkyl substituted with halogen, and X is bromine.

3. The method according to claim 2, wherein $R_3$ is trifluoromethyl.

4. The method according to claim 1, wherein the dyslipidemia is hyperlipidemia.

5. The method according to claim 1, wherein the fatty liver is non-alcoholic fatty liver.

6. A method for ameliorating or alleviating a metabolic disorder selected from the group consisting of obesity, diabetes, dyslipidemia, fatty liver, and insulin resistance syndrome, the method comprising administering to a subject in thereof a food composition comprising a compound represented by Formula 1 or a pharmaceutically acceptable salt thereof as an active ingredient:

Formula 1

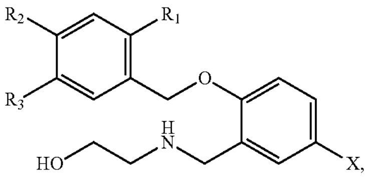

wherein $R_1$ and $R_2$ are each independently hydrogen or halogen, $R_3$ is hydrogen, halogen, or $C_1$-$C_3$ alkyl unsubstituted or substituted with halogen, and X is halogen.

7. The method according to claim 6, wherein, in Formula 1, $R_1$ is hydrogen, $R_2$ is fluoro, $R_3$ is $C_1$-$C_3$ alkyl substituted with halogen, and X is bromine.

8. The method according to claim 6, wherein $R_3$ is trifluoromethyl.

* * * * *